(12) United States Patent
Foreman

(10) Patent No.: US 9,693,767 B1
(45) Date of Patent: Jul. 4, 2017

(54) SUTURE PASSER INSTRUMENTS AND METHODS FOR THEIR USE

(76) Inventor: David Foreman, Lafayette, LA (US)

(*) Notice: Subject to any disclaimer, the term of this patent is extended or adjusted under 35 U.S.C. 154(b) by 287 days.

(21) Appl. No.: 13/547,236

(22) Filed: Jul. 12, 2012

Related U.S. Application Data

(60) Provisional application No. 61/559,362, filed on Nov. 14, 2011, provisional application No. 61/508,310, filed on Jul. 15, 2011.

(51) Int. Cl.
*A61B 17/04* (2006.01)
*A61B 17/06* (2006.01)

(52) U.S. Cl.
CPC .. *A61B 17/0469* (2013.01); *A61B 2017/0472* (2013.01); *A61B 2017/061* (2013.01); *A61B 2017/06042* (2013.01); *A61B 2017/06047* (2013.01); *A61B 2017/06052* (2013.01)

(58) Field of Classification Search
CPC ........ A61B 17/0469; A61B 2017/0472; A61B 2017/06042; A61B 2017/06047; A61B 2017/06052; A61B 2017/0608; A61B 2017/061; A61B 17/04
USPC ....... 606/139, 144, 148, 151, 185, 186, 213, 606/215, 232
See application file for complete search history.

(56) References Cited

U.S. PATENT DOCUMENTS

| | | | | |
|---|---|---|---|---|
| 659,422 | A * | 10/1900 | Shidler | 606/144 |
| 4,011,873 | A * | 3/1977 | Hoffmeister | 606/146 |
| 4,493,323 | A * | 1/1985 | Albright et al. | 606/144 |
| 4,627,437 | A * | 12/1986 | Bedi et al. | 606/220 |
| 4,730,615 | A * | 3/1988 | Sutherland et al. | 606/215 |
| 4,736,746 | A * | 4/1988 | Anderson | 606/220 |
| 5,342,374 | A * | 8/1994 | Wan et al. | 606/148 |
| 5,350,385 | A * | 9/1994 | Christy | A61B 17/0469 606/139 |
| 5,364,408 | A * | 11/1994 | Gordon | 606/144 |
| 5,391,182 | A * | 2/1995 | Chin | 606/213 |
| 5,462,560 | A * | 10/1995 | Stevens | 606/144 |
| 5,462,561 | A * | 10/1995 | Voda | 606/144 |
| 5,501,691 | A * | 3/1996 | Goldrath | 606/148 |
| 5,573,540 | A * | 11/1996 | Yoon | A61B 17/0469 606/139 |
| 5,722,981 | A * | 3/1998 | Stevens | 606/148 |
| 5,782,845 | A * | 7/1998 | Shewchuk | 606/144 |
| 5,897,563 | A * | 4/1999 | Yoon et al. | 606/144 |
| 6,283,979 | B1 * | 9/2001 | Mers Kelly et al. | 606/139 |
| 6,491,707 | B2 * | 12/2002 | Makower et al. | 606/157 |
| 7,438,208 | B2 * | 10/2008 | Larson | 227/175.1 |
| 7,846,179 | B2 * | 12/2010 | Belef et al. | 606/222 |
| 8,556,977 | B2 * | 10/2013 | Cauthen et al. | 623/17.16 |
| 2003/0004544 | A1 * | 1/2003 | Kawashima et al. | 606/222 |

(Continued)

*Primary Examiner* — Ryan J Severson
*Assistant Examiner* — Christian Knauss
(74) *Attorney, Agent, or Firm* — Hahn Loeser & Parks, LLP; Robert M. Gould

(57) ABSTRACT

A suture passer instrument is disclosed that contains two opposing needles positioned adjacent to each other on the end of a hollow handle. The needles are at least partially hollow and the hollow in the needles is of a sufficient size so that a suture can be passed through an entry point near the tip of the needles through the hollow of the needles to the hollow in the handle of the instrument. Two suture ports are located toward the sharp end of the needles such that when the needle pierces through tissue the suture can be grasped and its end pulled through the hollow central chamber of the device.

12 Claims, 6 Drawing Sheets

(56) References Cited

U.S. PATENT DOCUMENTS

Figure 1:
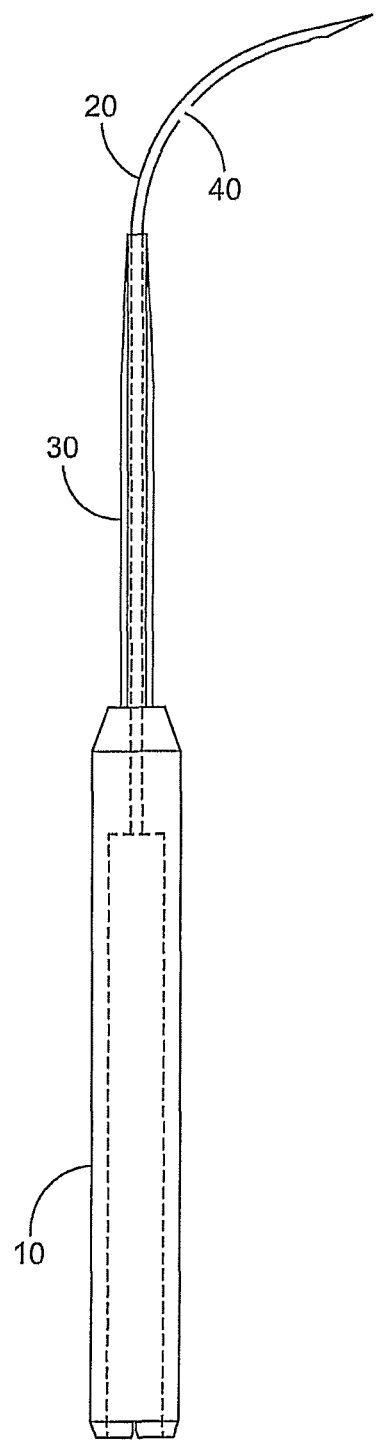

| | | | |
|---|---|---|---|
| 2003/0171764 A1* | 9/2003 | Debbas | 606/144 |
| 2004/0068273 A1* | 4/2004 | Fariss et al. | 606/144 |
| 2005/0113850 A1* | 5/2005 | Tagge | 606/151 |
| 2005/0222610 A1* | 10/2005 | Melker | 606/205 |
| 2005/0240147 A1* | 10/2005 | Makower et al. | 604/96.01 |
| 2006/0064115 A1* | 3/2006 | Allen et al. | 606/139 |
| 2006/0064116 A1* | 3/2006 | Allen et al. | 606/139 |
| 2006/0069398 A1* | 3/2006 | Suzuki et al. | 606/148 |
| 2007/0049970 A1* | 3/2007 | Belef et al. | 606/232 |
| 2007/0156245 A1* | 7/2007 | Cauthen et al. | 623/17.16 |
| 2007/0179509 A1* | 8/2007 | Nagata et al. | 606/144 |
| 2007/0282351 A1* | 12/2007 | Harada et al. | 606/138 |
| 2007/0293876 A1* | 12/2007 | Abe et al. | 606/144 |
| 2008/0065120 A1* | 3/2008 | Zannis | A61B 17/0401 606/144 |
| 2009/0043317 A1* | 2/2009 | Cavanaugh et al. | 606/144 |
| 2009/0143790 A1* | 6/2009 | Zucker et al. | 606/144 |
| 2009/0149882 A1* | 6/2009 | Tagge | 606/213 |
| 2009/0228041 A1* | 9/2009 | Domingo | 606/223 |
| 2009/0264905 A1* | 10/2009 | Funada | 606/146 |
| 2010/0076485 A1* | 3/2010 | Gonzales | A61B 17/0401 606/213 |
| 2010/0191259 A1* | 7/2010 | Suzuki et al. | 606/144 |
| 2011/0245850 A1* | 10/2011 | van der Burg et al. | 606/145 |
| 2011/0295258 A9* | 12/2011 | Bhatnagar et al. | 606/75 |

\* cited by examiner

SUTURE PASSER INSTRUMENTS AND METHODS FOR THEIR USE

BACKGROUND

Since the mid 1980s endoscopic sinus surgery has been the surgical method of choice in the United States for dealing with chronic sinusitis. But as with any surgery there can be complications. One common complication stems from post-operative laxity of middle turbinates, which allows the middle turbinate to move laterally during the healing phase and form adhesions to the lateral nasal wall ultimately resulting in scarring. This can ultimately result in closure of the very sinus cavity that the surgery was attempting to open.

Several strategies have been developed to prevent turbinate lateralization. For example, a standard needle and thread on a needle holder has been used to suture the middle turbinates medially to the septum of the nose. By doing this, the middle turbinates are fixated away from the lateral surgical field, in which they could adhere post-surgically thereby avoiding post surgical blocking. This technique is makeshift, cumbersome, time consuming, and difficult because of a lack of a simple delivery technique. 'Stapling' devices have also been used but those devices are too large and cumbersome to utilize effectively. An implantable device to secure the middle turbinate to the septum has also been tried but implants are also problematic in surgery. All techniques known thus far are frustratingly time consuming, cumbersome, obstructive of good visualization, and have therefore not been widely adopted by the surgical community.

New, easier and simpler devices and methods are needed for preventing the lateral movement of turbinates and the subsequent formation of scar tissue following endoscopic sinus surgery.

SUMMARY OF INVENTION

A new device and method for its use are disclosed that are simple and quick to use. A suture passer instrument is disclosed that contains two opposing needles positioned adjacent to each other on the end of a hollow handle. The needles are at least partially hollow and the hollow in the needles is of a sufficient diameter to allow for a suture to pass into the hollow in the handle of the instrument. The needles each have a suture port of sufficient size for the end of a suture to be introduced into the port and through the hollow of the needle and into the hollow of the handle. The suture port can be positioned in the vicinity of the pointed end of the needles. The needles can be curved to facilitate use. In embodiments having curved needles the suture ports can be positioned such that at least a portion of the suture port is on the concave side of the needle. The suture ports are advantageously located toward the sharp end of the needle such that once the needle pierces through tissue the suture can be grasped and its end pulled through the hollow central chamber of the device, removed through the suture port and cinched.

Also disclosed are surgical procedures that include the use of the disclosed suture passer instruments. The procedure involves passing one end of a suture through a suture port in one of the needles through the needle and into the hollow of the handle. The other end of the suture is also passed through the port of the opposing needle and into the hollow of the handle. The needles of the instrument can then be used to pierce through a tissue. Once the needles protrude through the tissue the suture ends can be withdrawn from the ports in the needles and cinched together. The procedure is particularly useful in nasal surgery where the needle can be used to pierce through the right middle turbinate, septum and left middle turbinate then cinched together so that the turbinates are held in a medial position. The procedure can be carried out during the initial stages of an endoscopic sinus surgery or afterwards.

The disclosed suture delivering instrument facilitates passage of a suture through the right middle turbinate, septum and left middle turbinate or any tissue in one pass. It is quick and relatively simple for experienced surgeons in comparison to the use of regular needles and sutures which is not only extremely difficult, but time consuming, and tissue traumatic in delivery.

FIGURES

FIG. 1 provides an illustration of a cross section of an embodiment of the suture passer instrument.

Figure 2:
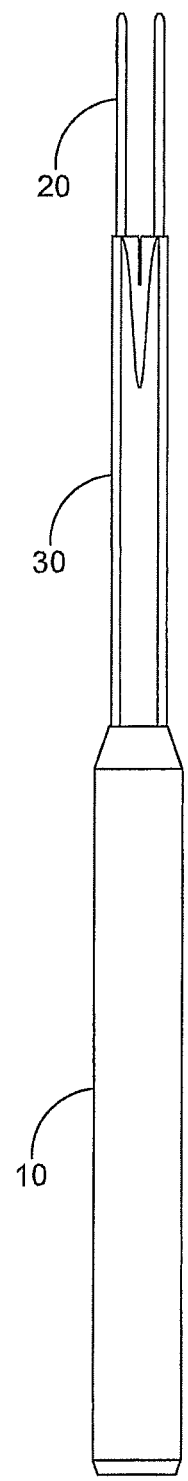

FIG. 2 provides an illustration of a side view of an embodiment of the suture passer instrument.

Figure 3:
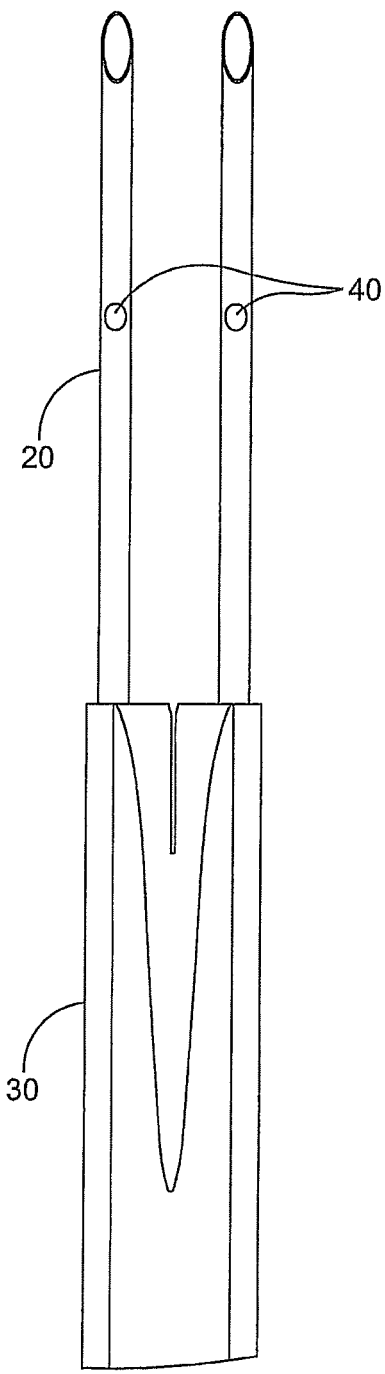

FIG. 3 provides an illustration of a top view of an embodiment of the suture passer instrument.

Figure 4:
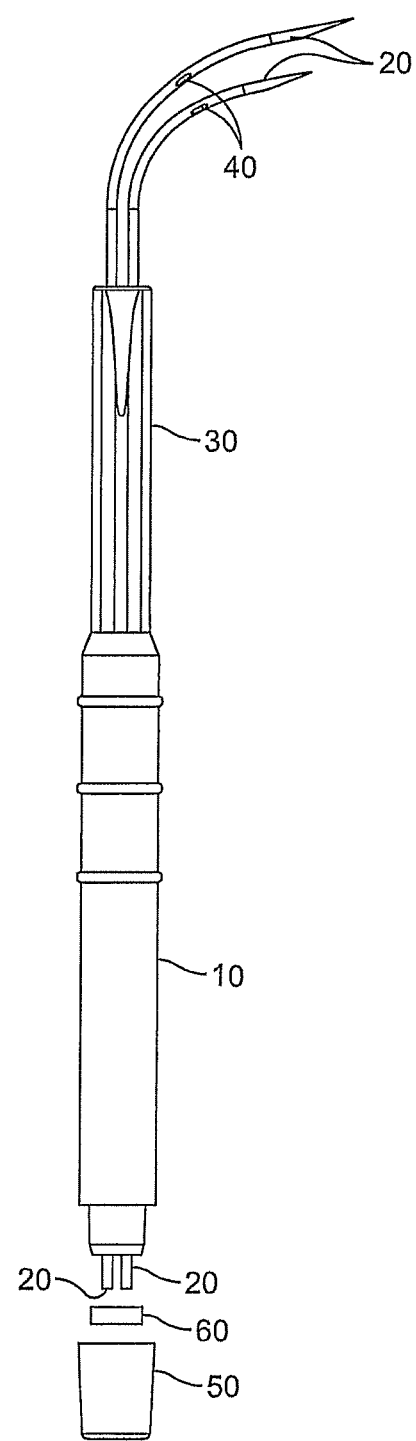

FIG. 4 provides an illustration of an embodiment of the suture passer instrument.

Figure 5:
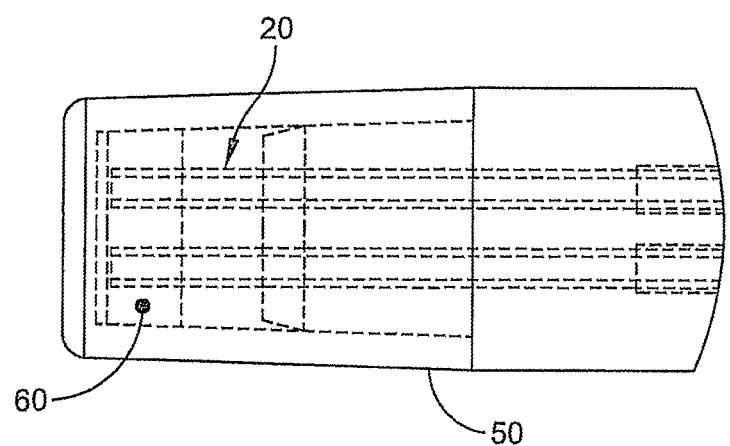

FIG. 5 provides an illustration of an embodiment of the end of the suture passer instrument.

Figure 6:
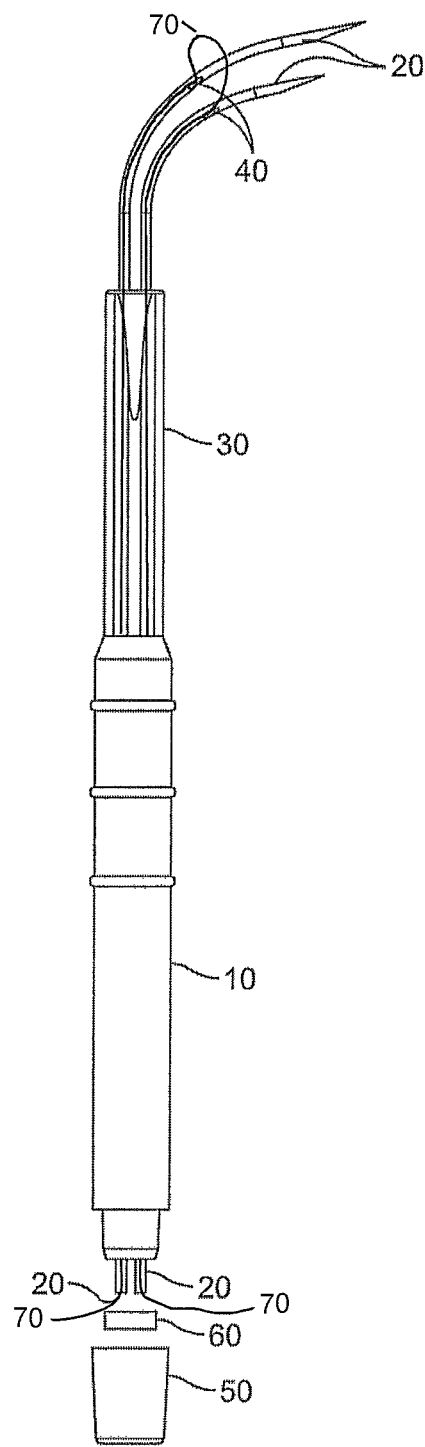

FIG. 6 provides an illustration of an embodiment as shown in FIG. 4 with a suture loaded into the suture passer instrument.

DETAILED DESCRIPTION OF INVENTION

Suture passer instruments and methods for using them are disclosed wherein, for example, during nasal surgery the needles of the suture passer instrument can be inserted in a single step through one turbinate, the septum, and the opposing turbinate to rapidly deliver a suture to opposite sides of the medial turbinate. The suture ends can then be removed from the instrument and tied such that middle turbinates are held in a medial position away from the scarring area for a prolonged period during the healing process.

The disclosed procedure can be performed before, during or after nasal surgery. Use of the procedure before nasal surgery has the advantage of improving visualization and access to the site of the surgery. Another advantage to the use of the procedure in nasal surgery is to facilitate post-operative sinus debridement, which is required several times following every surgery. Use of the procedure will also help to avoid the need for expensive sinus packing in many cases.

The suture passer instrument can be better understood by reference to the drawings. FIG. 1 provides a representative illustration of a cross section of the instrument. In general, the instrument contains a hollow handle 10 from which a set of curved needles 20 protrude through a sheath 30. A suture port 40 can be located on the concave side of each needle such that opposite ends of a suture can be introduced through port 40 on each needle and into the hollow center of handle 10.

The dimensions of the device can vary depending on the exact type of surgical procedure being used. The needle 20 and port 40 must be of sufficient size to allow for passage of suture ends into the handle of the device. For example, any needle that is a standard 18, 16 or 14 gauge, such as is manufactured by Vita Needle of Needham, Mass., can be used. More specifically 16 gauge needles could be used for nasal surgery and a suture port can be positioned, preferably on the concave side of the needles approximately 5 mm from the needle point such that the suture can be grasped once the tissue has been pierced and the needle protrudes through the tissue. Maintaining a physical hold of the suture in this manner will cause the ends of the suture to be released from the instrument through the suture ports as the instrument is withdrawn from the nasal passage. The curvature on the needle can be any suitable curvature that allows for the needle to be conveniently introduced into the nasal passage, or other desired tissue, and then pierce the turbinates and septum in a convenient manner. The dimensions of handle 10 and sheath 30 can also vary to facilitate convenient use of the instrument. The needles 20, handle 10 and sheath 30 can be made of any suitable material having sufficient strength to withstand the stresses encountered during surgery, cleaning and sterilization.

FIG. 2 provides a view from the top of the instrument. FIG. 3 provides an expanded view of the needles 20 and sheath 30 of the instrument.

FIG. 4 illustrates an alternative embodiment of the device in which needles 20 are in a vertical orientation with one needle extending past the other-beveled edge on the concave side of the needle. The needles can be positioned apart at any distance that allows them to be conveniently used to pierce the target tissues and conveniently deliver a suture. For example, the ends of the needle can be positioned from about 0.5 to about 1.5 cm and the needle points splayed apart by a range of about 0.5 to about 1.5 cm or more.

As shown best in FIG. 6 prior to use a suture 70 can be loaded into the instrument by passing each end of a suture 70 through the opposing suture ports 40 on the two needles. This allows, for example, a 15 inch suture strand, such as a standard 2-0 Vicryl suture by Ethicon, to be loaded with one end of the suture 70 being passed into each respective suture port 40, then into and through the hollow handle 10 and out the butt end of the instrument. This leaves the two ends of the suture exiting out the butt of the handle and an exposed 'loop' of suture between the two suture ports 40 of the needles. As illustrated in FIG. 6 a small cap 50 can be placed over the end with a foam sponge 60 to grasp the suture and prevent its subsequent outward migration during packaging and the manipulation of the device during surgery. With a suture loaded into the instrument, the instrument can then be used in surgery.

FIG. 5 illustrates the butt end of the device with protruding needles 20 abutted by foam sponge 60 covered by cap 50.

The instrument can be used in surgery, especially nasal surgery by introducing it into the right or left nasal cavity with needles pointed superiorly. Preferably this is carried out with nasal endoscopic visualization. Once the sharp end of the needles are lateral to the middle turbinate, the instrument is rotated so that the needles point into the turbinate. The middle turbinate is then penetrated with the needle complex, which is then in position to penetrate the septum. This procedure can advantageously be carried out after septoplasty because bone removal from the septum will facilitate passage of the needle through the septum. With the instrument in place the endoscope is shifted to the contralateral nasal cavity and with endoscopic visualization, the needles are then passed from a medial to a lateral position through the remaining contralateral middle turbinate.

At this point, with the design of the one pass suture passer, access to the ends of the suture is available. The suture can be removed by grasping the suture near suture port 40 and pulling each end out of the needle. The other side or loop of suture has been left in the initial nasal cavity side. The separation between the needles allows the soft tissue and bone to be grasped. The loose suture on the opposing nasal side is then cinched down and tied. This suture lasso effectively pulls the middle turbinates together in a medialized location against either side of the septum, which achieves the goals and advantages of the invention.

The invention claimed is:

1. A suture passer instrument comprising a device for medializing turbinates in nasal surgery having two at least partially hollow needles positioned adjacent to each other and curved in the same direction laterally relative to a longitudinal axis of the needles and positioned on an end of a hollow handle, wherein the hollow in the needles is in communication with the hollow in the handle, and the hollow in the needles and the handle is of sufficient diameter to allow a suture to pass there within and wherein the needles each have a sharp end and a port of sufficient size for ends of the suture to be introduced into the ports and through the hollow needle into the hollow of the handle, the suture passer instrument houses only the suture when ready for use to deliver the suture in surgery.

2. The suture passer instrument of claim 1, wherein the curve in the needles forms a concave side and the suture ports open on at least a portion of the concave side of the needles.

3. The suture passer instrument of claim 1, wherein the ports are located proximal to the sharp ends of the needles such that when the needles pierce a tissue the ends of the suture can be removed from the needles.

4. The suture passer instrument of claim 1, wherein the ends of the suture are located in the hollow handle and the suture extends between the suture ports in the needles.

5. The suture passer instrument of claim 1, wherein the needles are positioned in a parallel orientation.

6. A surgical procedure comprising the steps of obtaining the suture passer instrument of claim 1 and a suture, piercing a tissue with both needles, withdrawing ends of the suture from the suture ports and cinching the suture ends together.

7. The surgical procedure of claim 6, wherein the surgery is nasal surgery.

8. The surgical procedure of claim 6, wherein the surgery is nasal surgery and the tissue includes a middle turbinate.

9. The surgical procedure of claim 6, wherein the surgery is nasal surgery and the tissue includes a right middle turbinate, septum and left middle turbinate.

10. The surgical procedure of claim 6, wherein the surgery is nasal surgery and the tissue includes a right middle turbinate, septum and left middle turbinate and the suture holds the right and left middle turbinates in a medial position after cinching.

11. The surgical procedure of claim 6, wherein the surgery is nasal surgery and the tissue includes a right middle turbinate, septum and left middle turbinate and the procedure is carried out prior to endoscopic sinus surgery.

12. The surgical procedure of claim 6, wherein the surgery is nasal surgery and the tissue includes a right middle turbinate, septum and left middle turbinate and the procedure is carried out following endoscopic sinus surgery.

* * * * *